United States Patent [19]

Franckowiak et al.

[11] Patent Number: 4,886,804
[45] Date of Patent: Dec. 12, 1989

[54] CIRCULATION-ACTIVE DIHYDROPYRIDINE ETHERS

[75] Inventors: Gerhard Franckowiak; Martin Bechem; Rainer Gross, all of Wuppertal; Siegfried Hebisch, Oberhausen; Matthias Schramm, Cologne, all of Fed. Rep. of Germany

[73] Assignee: Bayer Aktiengesellschaft, Leverkusen, Fed. Rep. of Germany

[21] Appl. No.: 249,391

[22] Filed: Sep. 20, 1988

[30] Foreign Application Priority Data

Sep. 25, 1987 [DE] Fed. Rep. of Germany ..... 37323806

[51] Int. Cl.$^4$ ..................... A61K 31/50; C07D 237/04
[52] U.S. Cl. .................................. 514/252; 514/345; 544/238; 544/239; 546/290
[58] Field of Search ................ 544/238; 546/290, 291; 514/247, 252, 345

[56] References Cited

U.S. PATENT DOCUMENTS

| | | | |
|---|---|---|---|
| 3,495,964 | 2/1970 | Driscoll | 546/291 |
| 3,974,275 | 8/1976 | Bossert et al. | |
| 3,996,234 | 12/1976 | Bossert et al. | |
| 4,031,104 | 6/1977 | Bossert et al. | |
| 4,038,399 | 7/1977 | Bossert | 424/266 |
| 4,179,500 | 12/1979 | Junge | 536/1 |
| 4,248,873 | 3/1981 | Bossert | 544/238 |
| 4,514,400 | 4/1985 | Campbell | 544/238 |
| 4,532,248 | 7/1985 | Franckowiak | 514/345 |
| 4,686,229 | 8/1987 | Rosentretter | 544/238 |
| 4,742,068 | 5/1988 | Kukla | 544/238 |
| 4,753,936 | 6/1988 | Franckowiak | 544/357 |

FOREIGN PATENT DOCUMENTS

0206747 12/1986 European Pat. Off.
2218644 10/1973 Fed. Rep. of Germany.
2641746 3/1978 Fed. Rep. of Germany.

OTHER PUBLICATIONS

Chemical Abstracts vol. 80, 14958g, Bossert et al., abstracting DE 2,218,644 (1973).
Chemical Abstracts vol. 89, 44142q, Junge et al., abstracting DE. 2,641,746.
Chemical Abstracts vol. 106, 176173e, Sircar, abstracting EP 206,747 (1966).

*Primary Examiner*—Donald G. Daus
*Attorney, Agent, or Firm*—Sprung Horn Kramer & Woods

[57] ABSTRACT

Cardioactive novel dihydropyridine ethers of the formula

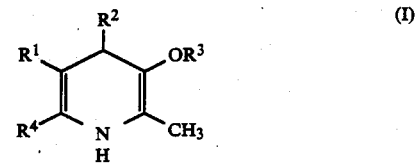

in which $R^1$ -stands for cyano, nitro or for a -COOR$^5$ group,
wherein $R^5$ -denotes straight-chain, branched or cyclic alkyl having up to 6 carbon atoms, which can be interrupted by an oxygen in the chain and which can be monosubstituted or polysubstituted by identical or different substituents from the group consisting of halogen, cyano, hydroxyl, phenyl, phenoxy or by a group of the formula

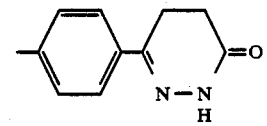

$R^2$ -stands for aryl having 6 to 12 carbon atoms, which can be monosubstituted, disubstituted or trisubstituted by identical or different substituents from the group consisting of halogen, cyano, nitro, trifluoromethyl, trifluoromethoxy, trifluoromethylthio, alkyl having up to 4 carbon atoms or alkoxy having up to 4 carbon atoms, $R^3$ -stands for aryl having 6 to 12 carbon atoms, or stands for straight-chain, branched or cyclic alkyl having up to 6 carbon atoms and $R^4$ -stands for straight-chain alkyl having up to 4 carbon atoms or for amino or a physiologically acceptable salt thereof.

12 Claims, No Drawings

CIRCULATION-ACTIVE DIHYDROPYRIDINE ETHERS

The invention relates to new dihydropyridine ethers, several processes for their preparation and their use in medicaments, in particular in circulation-influencing medicaments.

The present invention relates to new dihydropyridine ethers of the general formula (I)

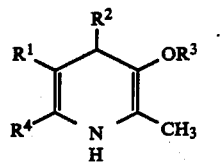

in which $R^1$ - stands for cyano, nitro or for a —COOR$^5$ group, wherein $R^5$ - denotes straight-chain, branched or cyclic alkyl having up to 6 carbon atoms, which can be interrupted by an oxygen in the chain and which can be monosubstituted or polysubstituted by identical or different substituents from the series comprising halogen, cyano, hydroxyl, phenyl, phenoxy or by a group of the formula

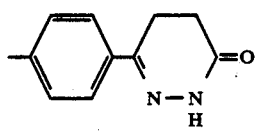

$R^2$ - stands for aryl having 6 to 12 carbon atoms, which can be monosubstituted, disubstituted or trisubstituted by identical or different substituents from the series comprising halogen, cyano, nitro, trifluoromethyl, trifluoromethoxy, trifluoromethylthio, alkyl having up to 4 carbon atoms or alkoxy having up to 4 carbon atoms, $R^3$ - stands for aryl having 6 to 12 carbon atoms, or stands for straight-chain, branched or cyclic alkyl having up to 6 carbon atoms and $R^4$ - stands for straight-chain alkyl having up to 4 carbon atoms or for amino and their physiologically acceptable salts.

Physiologically acceptable salts can be salts of the compounds according to the invention with inorganic or organic acids. Examples which may be mentioned are: hydrohalides such as, for example, hydrochlorides or hydrobromides, hydrogen sulphates, sulphates, hydrogen phosphates, phosphates, or acetates, maleates, fumarates, citrates, tartrates, lactates or benzoates.

The compounds according to the invention exist in stereoisomeric forms which either behave as image and mirror-image (enantiomers) or which do not behave as image and mirror-image (diastereomers). The invention relates both to the antipodes and the racemic forms as well as the diastereomer mixtures. The racemic forms, like the diastereomers, can be resolved into stereoisomerically uniform constituents in a known manner (compare E.L. Eliel, Stereochemistry of Carbon Compounds, McGraw Hill, 1962).

The compounds according to the invention are new and possess valuable pharmacological properties. They influence blood pressure and can therefore be employed for controlling circulatory disorders.

Preferred compounds of the general formula (I) are those in which $R^1$ - stands for nitro or for a —COOR$^5$ group, wherein $R^5$ - denotes straight-chain or branched alkyl having up to 4 carbon atoms, which can be interrupted by an oxygen atom in the chain and which can be substituted by a substituent from the series comprising fluorine, chlorine, bromine, cyano, hydroxyl, phenyl or by a group of the formula

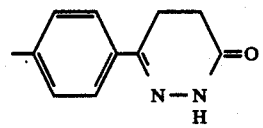

$R^2$ - stands for phenyl which can be monosubstituted or disubstituted by identical or different substituents from the series comprising fluorine, chlorine, bromine, nitro, trifluoromethyl, trifluoromethoxy, methyl or methoxy, $R^3$ - stands for phenyl, or for staight-chain or branched alkyl having up to 4 carbon atoms, and $R^4$ - stands for straight-chain alkyl having up to 4 carbon atoms or for amino, and their physiologically acceptable salts.

Particularly preferred compounds of the general formula (I) are those in which $R^1$ - stands for nitro or for a —COOR$^5$ group wherein $R^5$ - stands for straight-chain or branched alkyl having up to 3 carbon atoms, which can be substituted by a group of the formula

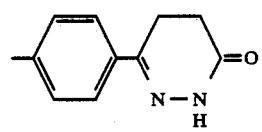

$R^2$ - stands for phenyl which can be monosubstituted or disubstituted by identical or different substituents from the series comprising chlorine, nitro or trifluoromethyl, $R^3$ - stands for phenyl or methyl, and $R^4$ - stands for methyl or for amino and their physiologically acceptable salts.

The compounds of the general formula (I) according to the invention in which $R^1$, $R^2$, $R^3$ and $R^4$ have the abovementioned meaning, are obtained by reacting [A] aldehydes of the general formula (II)

in which $R^2$ - has the abovementioned meaning and ketones of the general formula (III)

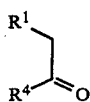 (III)

in which
R[1] and R[4] have the abovementioned meaning, or their Knoevenagel condensation produces (ylidene compounds) of the general formula (IV)

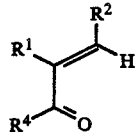 (IV)

in which
R[1], R[2] and R[4] have the abovementioned meaning, with enamines of the general formula (V)

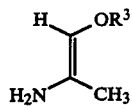 (V)

in which
R[3] has the abovementioned meaning in inert solvents, or

[B] aldehydes of the general formula (II) and ketones of the general formula (VI)

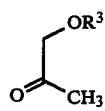 (VI)

in which
R[3] has the abovementioned meaning, or their ylidene compounds of the general formula (VII)

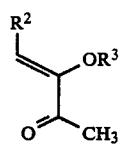 (VII)

in which
R[2] and R[3] have the abovementioned meaning, with ammonia and ketones of the general formula (III), or with enamines of the general formula (VIII)

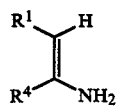 (VIII)

in which
R[1] and R[4] have the abovementioned meaning, in inert solvents.

Depending upon the type of starting material used, the synthesis variations A or B for the compounds according to the invention can be represented by the following equations:

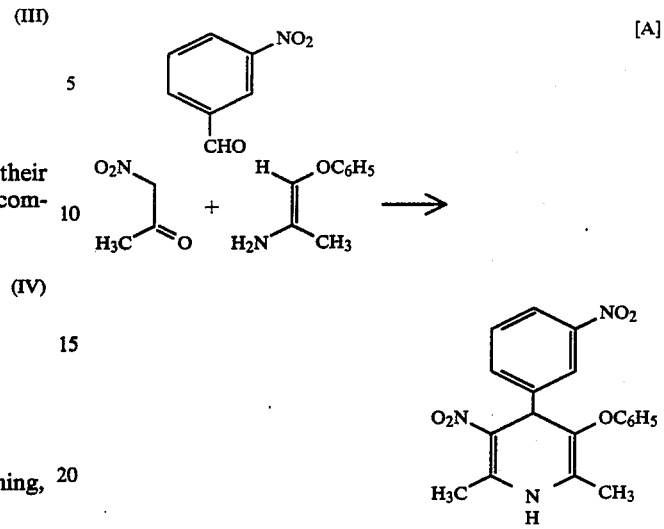

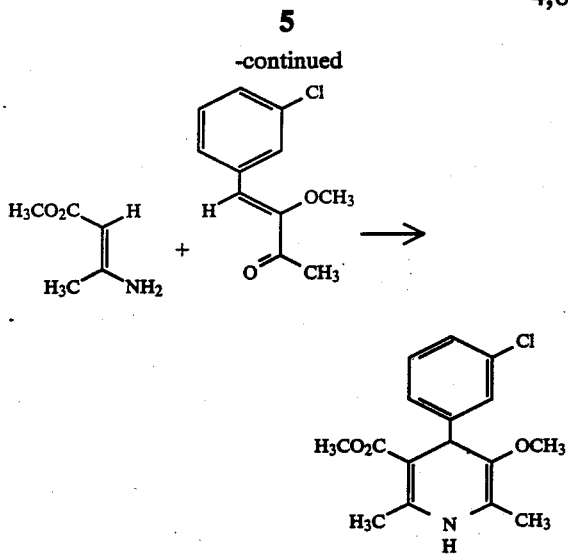

Suitable solvents are all inert organic solvents. These preferably include alcohols such as methanol, ethanol, propanol or isopropanol, or ethers such as diethyl ether, dioxane, tetrahydrofuran, glycol monomethyl ether or glycol dimethyl ether, or amides such as dimethylformamide or hexamethylphosphoric triamide, or glacial acetic acid, acetonitrile, dimethyl sulphoxide or pyridine. It is likewise possible to employ mixtures of the solvents mentioned.

The reaction temperatures can be varied within a relatively wide range. In general, the process is carried out between +20° C. and +150° C., preferably between +20° C. and +100° C., especially the boiling temperature of the particular solvent.

The reaction can be carried out at atmospheric pressure, but also at elevated or reduced pressure. In general, the reaction is carried out under atmospheric pressure.

In carrying out processes A and B according to the invention, the ratio of the substances taking part in the reaction is arbitrary. In general, the reaction is carried out using molar quantities of the reactants. However, it has also proved expedient to employ nitroacetone or the nitroacetone/ammonia addition product in an excess of up to 20 fold, preferably up to 10 fold.

The aldehydes of the general formula (II) employed as starting materials are known or can be prepared by known methods [E. Mosettig, Organic Reactions Vol. III, 218 (1954)].

The ketones of the general formula (III) employed as starting materials are known or can be prepared by known methods [D. Borrmann, Houben-Weyls "Methoden der organischen Chemie" (Houben-Weyl's "Methods of Organic Chemistry") Volume VII/4, 230 (1968); N. Levy and C. W. Scaife, J. Chem. Soc. (London) 1946, 1100; C. D. Hurd and M. E. Nilson, J. Org. Chem. 20, 927 (1955)].

The ketones of the general formula (VI) employed as starting materials are known or can be prepared by known methods [Tegnér, Acta Chem. Scand. 6, 782 (1952); Reppe et al., Liebigs Ann. Chem. 596, 1 (1955); D. Gauthier, Annales de Chimie [8] 16, 318; Stroemer et al., Chem. Ber. 28, 1253 (1895); St. Welin, Chem. Ber. 35, 3553 (1902)].

The enamines of the general formulae (V) and (VIII) employed as starting materials are known or can be prepared by known methods [F. A. Glickman and A. C. Cope, J. Am. Chem. Soc. 67, 1017 (1945); H. Boehme and K.-H. Weisel, Arch. Pharm. 310, 30 (1977)].

Some of the Knoevenagel condensation products of the formula (IV) (ylidene compounds) employed as starting materials are known or can be prepared by methods which are known per se [G. Jones, "The Knoevenagel Condensation" Organic Reactions XV, 204 (1967); A. Dornow and W. Sassenberg, Liebigs Ann. Chem., 602, 14 (1957)].

The ylidene compounds of the general formula (VII) employed as starting materials are known in part or can be prepared by known methods [W. Grell and H. Machleit, Liebigs Ann. Chem. 699, 53 (1966); V. Rosnati and A. Salimbeni, Gazz. Chim. Ital. 107, 271 (1977)].

The preceding preparation processes are only given for the purpose of illustration. The preparation of the compounds of the formula I is not limited to these processes, but any modification of these processes is utilizable in an identical manner for the preparation of the compounds according to the invention.

The compounds according to the invention influence the contractile force of the heart and the tone of the smooth musculature. They can therefore be employed in medicaments for influencing pathologically altered blood pressure, as coronary therapeutic and for the treatment of cardiac insufficiency. Moreover, they can be used for the treatment of cardiac dysrhythmias, for lowering the blood sugar, for detumescing mucous membranes and for influencing the salt and liquid balance.

The cardiac action was discovered in isolated guinea pig heart auricles.

For this, the left auricles of guinea pig hearts are isolated and suspended in an organ bath thermostated at 32° C. Krebs-Henseleit solution having the following composition (118.5 mmol/l of NaCl, 4.75 mmol/l of KCl, 1.19 mmol/l of $KH_2PO_4$, 119 mmol/l of $MgSO_4$, 25 mmol/l of $NaHCO_3$, 0.013 mmol/l of NaEDTA and 1.8 mmol/l of $CaCl_2$) is used as incubation medium with the addition of 10 mmol/l of glucose as an energy-supplying substance. The solution is aerated with a 95% $CO_2$, 5% $O_2$ mixture to maintain a pH value of 7.4. The left auricles are clamped in the organ bath, a definite basal tone is set and the tension is registered by means of a force transducer. With periodical electrical stimulation, the contractions resulting by this means are continuously recorded on a rapid recorder. In the presence of each of the compounds according to the invention, a percentage alteration compared to the starting value set at equal to 100% is obtained by this means:

| Example No. | Concentration | Percentage alteration of the contractile force |
|---|---|---|
| 5 | $10^{-2}$ | +23 |
| 7 | $10^{-2}$ | +30 |

The formulations are produced, for example, by extending the active compounds with solvents and/or excipients, if appropriate using emulsifiers and/or dispersants, where, for example, in the case of the use of water as a diluent, organic solvents can be used as auxiliary solvents if necessary.

Examples of auxiliaries which may be mentioned are: water, non-toxic organic solvents, such as paraffins (for example mineral oil fractions), vegetable oils (for example ground nut/sesame oil), alcohols (for example: ethyl alcohol, glycerol), excipients such as, for example, ground natural minerals (for example kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin, sulphite waste liquors, methyl cellulose, starch and polyvinylpyrrolidone) and lubricants (for example magnesium stearate, talc, stearic acid and sodium lauryl sulphate).

Administration takes place in a customary manner, preferably orally or parenterally, particularly perlingually or intravenously. In the case of oral administration, tablets can, of course, contain additives such as sodium citrate, calcium carbonate and dicalcium phosphate together with various additives, such as starch, preferably potato starch, gelatin and the like, in addition to the excipients mentioned. Furthermore, lubricants, such as magnesium stearate, sodium lauryl sulphate and talc can be used in addition for tabletting. In the case of aqueous suspensions, various flavor improvers or colorants can be added to the active compounds in addition to the abovementioned auxiliaries.

In the case of parenteral administration, solutions of the active compounds using suitable liquid excipients can be employed.

In general, it has proved to be advantageous to administer amounts of about 0.001 to 1 mg/kg, preferably about 0.01 to 0.5 mg/kg of body weight on intravenous administration to obtain effective results, and on oral administration the dosage is about 0.01 to 20 mg/kg, preferably 0.1 to 10 mg/kg of body weight.

Nevertheless, it may in some cases be necessary to deviate from the amounts mentioned, and in particular to do so as a function of the body weight or the type of administration route, the individual behavior towards the medicament, the nature of its formulation and the point in time or interval at which the administration takes place. Thus, it may be sufficient in some cases to manage with less than the abovementioned minimum amount, whereas in other cases the upper limit mentioned must be exceeded. In the case of administration of larger amounts, it may be advisable to divide these into several individual doses over the day.

PREPARATION EXAMPLES

Example 1
1-Diethylphosphono-1-methoxyacetone $$(H_5C_2O)_2\overset{O}{\overset{\|}{P}}-\underset{OCH_3}{\overset{}{C}H}-CO-CH_3$$

2 mols of acetyl bromide are added dropwise at a maximum of 60° C. to 2 mols of 1,1-dimethoxyacetone and the mixture is stirred for 1 hour more at 60° C. The 1-bromo-1-methoxy-acetone is distilled in vacuo (55%/11 torr); 271 g are obtained, to which 1.614 mols of triethyl phosphite are added dropwise. Ethyl bromide is then removed by distillation for 1 hour at 120° C. and 1 hour at 140° C. The residue is distilled in an oil pump vacuum (88° C./0.05 torr) (Ann. Chem. 696, 59 (1966))

Yield: 280.4 g (62.5% of theory)

Example 2

2-Methoxy-1-(2-trifluoromethylphenyl)but-1-en-3-one 0.102 mol of the product from Example 1 is added dropwise in the course of 0.5 hour to a suspension of 0.106 mol of sodium hydride in 200 ml of absolute dioxane, the mixture is stirred for a further 0.5 hours and 0.100 mol of o-trifluoromethylbenzaldehyde is then added dropwise at room temperature with cooling. The mixture is stirred for a further 3 hours, 2 ml of water in 20 ml of dioxane are added, the solvent is removed by evaporation in vacuo and the residue is fractionated in an oil pump vacuum. b.p.: 60°–65° C. (0.01 torr)

Yield: 12.2 g (50% of theory)

According to NMR, the product exists as a cis/trans mixture in a ratio of 2:3.

Example 3

1,4-Dihydro-2,6-dimethyl-3-methoxy-5-nitro-4-(2-trifluoromethylphenyl)pyridine

A total of 0.15 mol of nitroacetone/ammonia adduct is added in portions over 4 hours to 50 mmol of the product from Example 2 in 30 ml of isopropanol at 60° C. The mixture is stirred at 60° C. for a further 4 hours. The solvent is subsequently removed by rotatary evaporation and the residue is chromatographed on silica gel using chloroform. The combined product fractions are recrystallized from isopropanol/petroleum ether 1:1.

Yield: 2.6 g (16% of theory)

m.p.: 201° C.

Example 4

2-Amino-1-phenoxy-propene 0.2 mol of phenoxyacetone in 200 ml of tetrahydrofuran is saturated at reflux temperature with ammonia gas with the addition of 0.2 g of p-toluene sulphonic acid. The mixture is allowed to stand at room temperature for 24 hours and the solvent is then removed by evaporation in vacuo. The evaporation residue is employed crude in the reaction of Example 5B.

Example 5

1,4-Dihydro-2,6-dimethyl-5-nitro-3-phenoxy-4-phenylpyridine

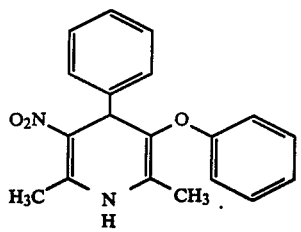

(A) 30 mmol of nitroacetone/ammonia addition compound are added in portions to 10 mmol of 2-phenoxy-1-phenyl-but-1-en-3-one (prepared analogously to Example 3) in 30 ml of isopropanol at 40° C. The mixture is heated at 60° C. for 1 hour and at reflux for 8 hours with the addition of 1 ml of aqueous ammonia. The solvent is removed by evaporation and the residue is chromatographed on silica gel using chloroform.

Yield: 12% of theory
m.p.: resin (B) 25 mmol of crude 2-amino-1-phenoxy-propene are added to 20 mmol of 2-nitro-1-phenyl-but-1-en-3-one in 50 ml of isopropanol and the mixture is stirred at 60° C. for 8 hours. The solvent is removed by evaporation and the residue is chromatographed on silica gel using chloroform.

Yield: 15% of theory
m.p.: resin

Example 6
2-Phenoxy-1-(2-trifluoromethyl-phenyl)but-1-en-3-one

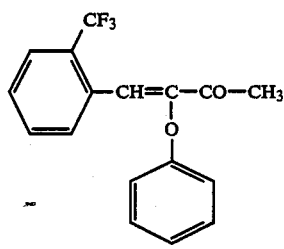

0.2 mol of phenoxyacetone and 0.25 mol of o-trifluoromethylbenzaldehyde are intensively stirred with 16 g of sodium hydroxide in 8 l of degassed water for 3 days with the exclusion of air. The batch is shaken with methylene chloride, and the organic phase is dried, evaporated, digested with petroleum ether and then recrystallized from ethanol.

Yield: 45.2% of theory
m.p.: 89° C.

Example 7
1,4-Dihydro-2,6-dimethyl-5-nitro-3-phenoxy-4-(2-trifluoromethylphenyl)pyridine

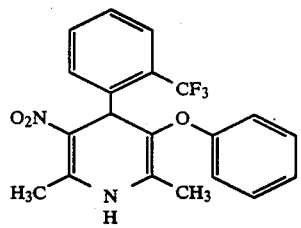

The title compound is obtained from 2-phenoxy-1-(2-trifluoromethylphenyl)-but-1-en-3-one and nitroacetone/ammonia addition compound after chromatography on silica gel analogously to Example 6.

Yield: 18% of theory
m.p.: 123° C.

Example 8
4-Oxo-4-[4-(tetrahydropyran-2-yl-oxymethyl)-phenyl]-butyric acid

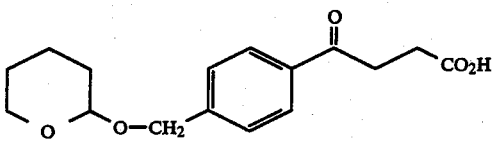

12.75 g (0.53 mol) of magnesium turnings in 200 ml of tetrahydrofuran are activated with a little iodine under protective gas, then 135 g of p-bromobenzyl tetrahydropyranyl ether are slowly added dropwise. The reaction proceeds strongly exothermically. The mixture is stirred for a further 2 hours with warming to complete the reaction. The solution is cooled to −80° C. and 53 g of succinic anhydride, suspended in 200 ml of tetrahydrofuran, are added in portions. The mixture is stirred for a further 2 hours, then hydrolyzed using 4 l of water and the pH is adjusted to 8 using 2 N sodium hydroxide solution. The mixture is washed with methylene chloride. The aqueous phase is adjusted to pH 4.5 using citric acid. The product is extracted using methylene chloride, dried and precipitated by the addition of petroleum ether.

Yield: 59 g (40.4% of theory)
m.p.: 97° C.

Example 9
4-(6-Oxo-1,4,5,6-tetrahydropyridazin-3-yl)benzyl alcohol

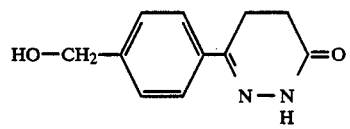

50 g of 4-oxo-4-[4-(tetrahydropyran-2-yl-oxymethyl)-phenyl]-butyric acid are suspended in 240 ml of water and the mixture is stirred at 90° C. for 3 hours with 10 ml of hydrazine hydrate. After cooling, the precipitated crystals are filtered off with suction. These crystals are dissolved in 500 ml of tetrahydrofuran and 100 ml each of glacial acetic acid, 1N hydrochloric acid and water are added. The mixture is allowed to stand at room temperature for 24 hours, the tetrahydrofuran is removed by distillation and the residue is extracted using methylene chloride. The product is already partly precipitated in this way and is filtered off with suction. The methylene chloride phase is worked up. Both crystallizates are impure.

Yield: 22.7 g (64% of theory)
m.p.: 188° C.

Example 10
4-(6-Oxo-1,4,5,6-tetrahydropyridazin-3-yl)benzyl β-aminocrotonate

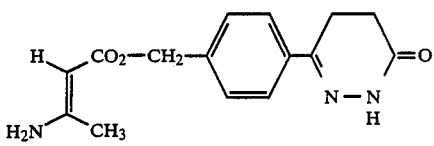

20 g of 4-(6-oxo-1,4,5,6-tetrahydropyridazin-3-yl)benzyl alcohol are suspended in 50 ml of tetrahydrofuran and reacted under reflux with 10.7 g of diketene after addition of 100 mg of 4-dimethylaminopyridine. The mixture is allowed to react for a further 2 hours, saturated with ammonia gas at reflux temperature and allowed to cool overnight, the tetrahydrofuran is removed by evaporation and the residue is boiled with isopropanol.

Yield: 17.5 g (92% of theory)
m.p.: 183° C.

Example 11
4-(6-Oxo-1,4,5,6-tetrahydropyridazin-3-yl)benzyl 1,4-dihydro-2,6-dimethyl-5-phenoxy-4-(2-trifluoromethylphenyl)-pyridine-3-carboxylate

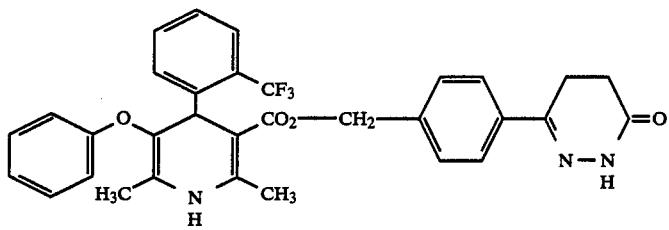

10 mmol of 2-phenoxy-1-(2-trifluoromethylphenyl)-but-1-ene-3-one and 10 mmol of 4-(6-oxo-1,4,5,6-tetrahydropyridazin-3-yl)benzyl 3-aminocrotonate are heated to reflux for 6 hours in 20 ml of isopropanol. The crude evaporation residue is chromatographed on silica gel using chloroform plus 6% methanol.

m.p.: 168° C.
Yield: 8% of theory

Example 12
Ethyl 2-amino-1,4-dihydro-6-methyl-5-phenoxy-4-phenylpyridine-3-carboxylate

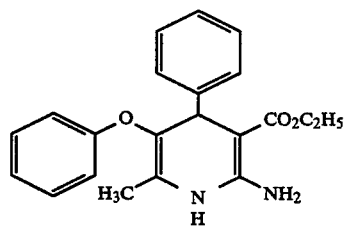

A solution of 25 mmol of ethyl amidinoacetate hydrochloride and 25 mmol of sodium methoxide in 20 ml of ethanol are added dropwise to 10 mmol of 3-phenoxy-1-phenyl-but-1-en-3-one in 20 ml of ethanol at reflux temperature. The mixture is heated to reflux for a further 2 hours, the solvent is removed by evaporation and the crude product is chromatographed on silica gel using chloroform. The product is isolated as a resin. Yield: 6% of theory It will be appreciated that the instant specification and claims are set forth by way of illustration and not limitation, and that various modifications and changes may be made without departing from the spirit and scope of the present invention.

What is claimed is:

1. A dihydropyridine ether of the formula

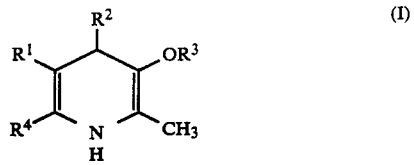

in which
$R^1$ - stands for cyano, nitro or for a —$COOR^5$ group, wherein
$R^5$ - denotes straight-chain or branched alkyl having up to 6 carbon atoms, which can be interrupted by an oxygen in the chain and which can be monosubstituted or polysubstituted by identical or different substituents from the group consisting of halogen, cyano, hydroxyl, phenyl, phenoxy and

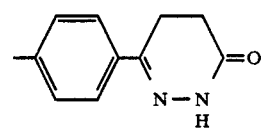

$R^2$ - stands for aryl having 6 to 12 carbon atoms, which can be monosubstituted, disubstituted or trisubstituted by identical or different substituents from the group consisting of halogen, cyano, nitro, trifluoromethyl, trifluoromethoxy, trifluoromethylthio, alkyl having up to 4 carbon atoms or alkoxy having up to 4 carbon atoms, $R^3$ - stands for aryl having 6 to 12 carbon atoms, or stands for straight-chain, branched or cyclic alkyl having up to 6 carbon atoms and $R^4$ - stands for straight-chain alkyl having up to 4 carbon atoms or for amino or a physiologically acceptable salt thereof.

2. A compound or salt according to claim 1, in which:
$R^1$ - stands for nitro or for a —$COOR^5$ group, wherein
$R^5$ - denotes straight-chain or branched alkyl having up to 4 carbon atoms, which can be interrupted by an oxygen atom in the chain and which can be substituted by a substituent from the group consisting of fluorine, chlorine, bromine, cyano, hydroxyl, phenyl and R[2] - stands for phenyl which can be monosubstituted or disubstituted by identical or different substituents from the group consisting of fluorine, chlorine, bromine, nitro, trifluoromethyl, trifluoromethoxy, methyl or methoxy, R[3] - stands for phenyl, or for straight-chain or branched alkyl having up to 4 carbon atoms, and R[4] - stands for straight-chain alkyl having up to 4 carbon atoms or for amino.

3. A compound or salt according to claim 1, in which

R[1] - stands for nitro or for a —COOR[5] group wherein

R[5] - stands for straight-chain or branched alkyl having up to 3 carbon atoms, which can be substituted by a group of the formula R[2] - stands for phenyl which can be monosubstituted or disubstituted by identical or different substituents from the group consisting of chlorine, nitro or trifluoromethyl, R[3] - stands for phenyl or methyl, and R[4] - stands for methyl or for amino.

4. A compound according to claim 1, wherein such compound is 1,4-dihydro-2,6-dimethyl-3-methoxy-5-nitro-4-(2-trifluoromethylphenyl)pyridine of the formula or a physiologically acceptable salt thereof.

5. A compound according to claim 1, wherein such compound is 1,4-dihydro-2,6-dimethyl-5-nitro-3-phenoxy-4-phenylpyridine of the formula or a physiologically acceptable salt thereof.

6. A compound according to claim 1, wherein such compound is 1,4-dihydro-2,6-dimethyl-5-nitro-3-phenoxy-4-(2-trifluoromethylphenyl)-pyridine of the formula or a physiologically acceptable salt thereof.

7. A compound according to claim 1, wherein such compound is 4-(6-oxo-1,4,5,6-tetrahydropyridazin-3-yl)-benzyl 1,4-dihydro-2,6-dimethyl-5-phenoxy-4-(2-trifluoromethylphenyl)-pyridine-3-carboxylate of the formula or a physiologically acceptable salt thereof.

8. A compound according to claim 1, wherein such compound is ethyl 2-amino-1,4-dihydro-6-methyl-5-phenoxy-4-phenylpyridine-3-carboxylate of the formula or a physiologically acceptable salt thereof.

9. A cardioactive composition comprising a cardioactive amount of a compound or salt according to claim 1 and a physiologically acceptable carrier.

10. A composition according to claim 9 in the form of a tablet, capsule or ampule.

11. A method of increasing the blood pressure, of treating cardiac insufficiency or dysrhythmia or for lowering blood sugar in a patient in need thereof which comprises administering to such patient an amount effective therefor of a compound or salt according to claim 1.

12. The method according to claim 11, wherein such compound is 1,4-dihydro-2,6-dimethyl-3-methoxy-5-nitro-4-(2-trifluoromethylphenyl)pyridine, 1,4-dihydro-2,6-dimethyl-5-nitro-3-phenoxy-4-phenylpyridine, 1,4-dihydro-2,6-dimethyl-5-nitro-3-phenoxy-4-(2-trifluoromethylphenyl)-pyridine, 4-(6-oxo-1,4,5,6-tetrahydropyridazine-3-yl)-benzyl 1 1,4-dihydro-2,6-dimethyl-5-phenoxy-4-(2-trifluoromethylphenyl)-pyridine-3-carboxylate, or ethyl 2-amino-1,4-dihydro-6-methyl-5-phenoxy-4-phenyl-pyridine-3-carboxylate.

* * * * *